United States Patent [19]

Virnig

[11] Patent Number: 4,612,403
[45] Date of Patent: Sep. 16, 1986

[54] HYDROFORMYLATION OF OLEFINIC COMPOUNDS IN THE PRESENCE OF A COBALT CATALYST AND AN ORGANIC NITRILE PROMOTER

[75] Inventor: Michael J. Virnig, Fridley, Minn.

[73] Assignee: Henkel Corporation, Minneapolis, Minn.

[21] Appl. No.: 747,149

[22] Filed: Jun. 20, 1985

[51] Int. Cl.$^4$ .................. C07C 45/50; C07C 27/22
[52] U.S. Cl. ......................... 568/454; 568/455; 568/902; 568/909
[58] Field of Search ............... 568/455, 454, 909, 902

[56] References Cited

U.S. PATENT DOCUMENTS

| | | | |
|---|---|---|---|
| 2,820,059 | 1/1958 | Hasek et al. | 568/455 |
| 2,834,812 | 5/1958 | Hughes et al. | 568/455 |
| 3,231,621 | 1/1966 | Slaugh | 568/455 |
| 3,627,843 | 12/1971 | Pregaglia | 568/455 |
| 3,931,332 | 1/1976 | Wilkes | 568/455 |

FOREIGN PATENT DOCUMENTS

| | | | |
|---|---|---|---|
| 2210937 | 10/1972 | Fed. Rep. of Germany | 568/455 |
| 1668484 | 3/1978 | Fed. Rep. of Germany | 568/455 |
| 1564932 | 3/1969 | France | 568/455 |

Primary Examiner—Werren B. Lone
Attorney, Agent, or Firm—Ernest G. Szoke; Patrick J. Span

[57] ABSTRACT

A process is provided for the hydroformylation of an olefinic compound with carbon monoxide and hydrogen in the presence of cobalt catalyst and a promoter comprised of an organic nitrile. In one aspect, the olefinic compounds are olefinic fatty compounds with at least 4 carbon atoms. In another aspect, the cobalt catalyst consists of only a soluble cobalt salt and a promoter consisting of an organic nitrile such as acetonitrile. In another aspect of the invention, the olefinic compound to be hydroformylated contains a cyano substituent such that the reaction is self promoted.

15 Claims, No Drawings

HYDROFORMYLATION OF OLEFINIC COMPOUNDS IN THE PRESENCE OF A COBALT CATALYST AND AN ORGANIC NITRILE PROMOTER

FIELD OF THE INVENTION

This invention relates to an improved process for the hydroformylation of olefinic compounds using an improved promoted catalyst system. More particularly, this invention relates to the use of a cobalt catalyst and an organic nitrile promoter in the hydroformylation of olefinic compounds.

BACKGROUND OF THE INVENTION

U.S. Pat. No. 3,627,843, to Pregaglia et al., discloses an improved process for preparing butyric aldehydes by hydroformylation of propene in the presence of cobalt-carbonyls complexed with phosphines, wherein the reaction medium is chosen from among N,N-dialkylamides, tetra-alkylureas, aliphatic nitriles, and dinitriles.

An article entitled "OXO PROCESS" in Kirk-Othmer, *Encyclopedia of Chemical Technology*, pp. 637-653, (3rd ed.), discloses that these organophosphines improve the selectivity of a cobalt catalyst to the straight chain alcohol, but lowers the overall activity of the catalysts. (see pp. 638-639)

U.S. Pat. No. 3,806,538, to Prognon et al., discloses a process for the total separation and direct recycling of the catalyst from the hydroformylation of olefins such as propene and cyclohexane by carbon monoxide and hydrogen, said catalysts consisting of octa- or hydrocarbonyls of cobalt, optionally containing phosphorous containing promoters such as phosphites and phosphines, in which the catalyst is separated from the reaction products by insolubilization by means of hydrocyanic acid or cyanohydrins, wherein the complex cobalt cyanocarbonyl, possibly with the combined phosphorous compound, is then recycled in the hydroformylation process.

U.S. Pat. No. 4,219,684, to Imai, discloses that alcohols may be synthesized by reacting an olefinic compound, carbon monoxide and hydrogen in the presence of a Group VIII organometallic complex catalyst and a promoter compound comprising a nitrile. The patent discloses octadecenes as examples of olefinic hydrocarbons, discloses rhodium, rhodium salts and rhodium phosphene and phosphite complexes as examples of the catalysts, and discloses acetonitrile and tridecylcyanide as examples of promoters.

U.S. Pat. No. 4,299,777, to Garron et al., discloses the preparation of cyano acetals by the reaction of an alcohol, a nitrile, carbon monoxide, and hydrogen in the presence of a cobalt carbonyl catalyst and an effective amount of a cyano alkyl amine or carboxy alkyl amine promoter.

U.S. Pat. No. 4,216,343, to Rogier, discloses the hydroformylation of unsaturated fatty alcohols with carbon monoxide and hydrogen in the presence of a rhodium catalyst. The patent states that higher yields of product are obtained through the use of rhodium catalysts then if a cobalt catalyst is employed and that a much higher degree of isomerization of the double bond occurs with a cobalt catalyst then with a rhodium catalyst.

SUMMARY OF THE INVENTION

This invention relates to a process of hydroformylation of an olefinic fatty compound comprising reacting an olefinic fatty compound having at least 4 carbon atoms with carbon monoxide and hydrogen in the presence of a catalyst and a promoter comprised of an organic nitrile. As used herein, the term "olefinic fatty compound" shall be used to refer to compounds having a straight chain or branched hydrocarbon structure and which also contain an ethylenic unsaturation. Also as used herein, the term "organic nitrile" shall be used to refer to any hydrocarbon compound containing a cyano substituent.

This invention also relates to a composition useful as a catalyst in the hydroformylation of an olefinic fatty compound comprising cobalt and an organic nitrile selected from the group consisting of cyano-substituted alkanes having from 2 to 44 carbon atoms and cyano-substituted alkenes having from 4 to 22 carbon atoms.

This invention also relates to a process for the hydroformylation of an olefinic compound comprising reacting an olefinic compound with carbon monoxide and hydrogen in the presence of a catalyst consisting of soluble cobalt salt and a promoter consisting of cyano-substituted alkanes having from 2 to 44 carbon atoms and cyano-substituted alkenes having from 4 to 22 carbon atoms. As used herein, the term olefinic compound shall be used to refer to any organic hydrocarbon which contains an ethylenic unsaturation.

This invention also relates to a composition useful as the catalyst in the hydroformylation of an olefinic compound consisting of a soluble cobalt salt and an organic nitrile such as from the group consisting of cyano-substituted alkanes having from 2 to 44 carbon atoms and cyano-substituted alkenes having from 4 to 22 carbon atoms.

It has been found that the processes and compositions of this invention allow for the use of a cobalt catalyst having greater activity then a rhodium catalyst and, surprisingly, greater selectivity for the hydroformyl product, i.e. less bond migration and simple hydrogenation of the olefin to yield a product substantially equal or superior to the product obtained by the use of a more expensive rhodium catalyst.

DETAILED DESCRIPTION OF THE INVENTION

Examples of the olefinic compounds which may be used as starting materials in the process of this invention will include straight chain and branched chain olefins containing from 2 to about 30 carbon atoms. Examples include the simple alkenes such as ethylene, propylene, 1-butene, 2-butene, 1-pentene, 2-pentene, 2-methyl-1-butene, 1-hexene, 2-hexene, 3-hexene, 2-methyl-1-pentene, 3-methyl-1-pentene, 1-heptene-2-heptene, 3-heptene, 1-octene, 2-octene, 2-methyl-1-heptene, 3-methyl-1-heptene, 3-methyl-2-heptene, 3-octene, 4-octene, 1-nonene, 2-nonene, 3-nonene, 4-nonene, as well as the corresponding isomers of decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, n-triacontenes. These olefins also include cyclic olefins such as cyclopentene, cyclohexene, and cycloheptene. The olefinic compounds also include aromatic alkenes such as styrene, alphamethylstyrene and vinyltoluene. These olefinic compounds also include olefins substituted with a variety of substituents including those selected from the group consisting of hydroxyl, cyano, carboxyalkoxy, alkoxy, cyano-substituted alkoxy, and carboxyalkoxy-substituted alkoxy.

Preferred examples of the olefinic compounds are the olefinic fatty compounds having at least 4 carbon atoms which are straight chain or branched alkenes which may have any of the substituents described above. The preferred olefinic fatty compounds preferably have at least 7 carbon atoms, more preferably at least 9 carbon atoms and most preferably at least 14 carbon atoms. Specific examples of such compounds are the olefinic fatty compounds disclosed in U.S. Pat. Nos. 4,216,343, 4,216,344, 4,229,562, 4,304,945 and 4,356,128, all to Rogier, incorporated herein by reference. Specific examples of preferred olefinic fatty compounds include oleyl alcohol, oleonitrile, N,N-dimethyloleamide, N-methyl-N-acetyloleamide, methyl oleate, N-oleyoyl morpholine and the like.

The organic nitriles that are useful as a catalyst promoter for the process of this invention are cyano-substituted hydrocarbons, examples of which include alkyl nitriles, alkyl dinitriles, alkenyl nitriles and aromatic nitriles. Specific examples of these compounds include acetonitrile, propionitrile, butyeronitrile, valeronitrile, capronitrile, and n-enanthylonitrile, caprylonitrile, octacyanide, nonylcyanide, decylcyanide, undecylcyanide, dodecylcyanide, tridecylcyanide, oxalylnitrile, malononitrile, succinonitrile, glutaronitrile, adiponitrile, suberonitrile, axelonitrile, acrylonitrile, crotononitrile, isocrotonitrile, tiglonitrile, angelonitrile, benzonitrile, 2-methylbenzonitrile, 3-methylbenzonitrile, 4-methylbenzonitrile, dimethylacetonitrile, diethylacetonitrile, diphenylacetonitrile, dimethypropionitrile, diethylpropionitrile, diphenylpropionitrile, dimethylbutyronitrile, diethylbutyronitrile, diphenylbutyronitrile, dimethylsuccinonitrile, diethylsuccinonitrile, diphenylsuccinonitrile, and the like.

The organic nitrile may also contain substituents in addition to the cyano substituent, such as hydroxyl, halocarboxyalkoxy, carboxydialkylamino, carboxyacylamino, carboxy-N-acyl-N-alkyl amino, alkoxy, cyano-substituted alkoxy, carboxy-alkoxy-substituted, and carboxydialkyamino-substituted alkoxy.

Particularly preferred organic nitriles are selected from the group consisting of cyano-substituted alkanes having from 2 to 44 carbon atoms, and cyano-substituted alkenes having from 4 to 22 carbon atoms and which contain no other substituents.

In one aspect of this invention, the olefinic fatty compound to be hydroformylated may also contain a cyano substituent such that the olefinic compound is also an organic nitrile which can act as a promoter in accordance with this invention. One embodiment within this aspect of this invention is the hydroformylation of oleonitrile which is both an olefinic fatty compound and an organic nitrile in accordance with this invention.

The catalyst useful in this invention is a cobalt catalyst. Suitable sources of cobalt include the soluble cobalt salts such as cobalt nitrate, cobalt chloride, cobalt bromide, cobalt iodide, cobalt fluoride, and cobalt acetate as well complexes thereof such as the carbonyl complexes. Particularly preferred are the simple cobalt salts such as cobalt acetate which are relatively inexpensive and yet have excellent activity and selectivity in the process of this invention.

The cobalt catalyst is conveniently employed in catalytic amounts, based upon its metal content, preferably from about 20 ppm to about 10,000 ppm, most preferably from about 50 ppm to about 500 ppm by weight of the olefinic fatty compound. The organic nitrile promoter is conveniently employed in a mole ratio of organic nitrile to cobalt content of the catalyst of from about 200:1 to about 1:200, preferably from about 150:1 to about 1:10 and most preferably at about 100:1.

EXAMPLES

Preparation of 9(10)-Formyloctadecan-1OL

Example 1(a)

The following materials were charged to a one liter 316 SS Autoclave: 400 g of cis-9-octadecen-1-ol, (available as Oceanol 90/95 from Henkel KGaA which contains 3–4% hexadecanol and octadecanol), 77 g (1.88 mole) of acetonitrile, and 4.23 g (0.017 mole) of cobalt (II) acetate tetrahydrate.

The autoclave was then thoroughly purged with nitrogen. The autoclave was then pressurized to 2250 psig with a hydrogen-carbon monoxide (1:1) mixture and heated to 150° C. Gas uptake was essentially complete within 45 minutes. After gas uptake ceased completely, the autoclave was cooled and the crude product, weighing 543.6 g, was transferred to a flask containing 250 ml of heptane, 1.71 g of sodium bicarbonate, 500 ml of water, and 100 ml of methanol. The mixture was thoroughly mixed and then allowed to separate. The aqueous phase was discarded. The organic phase was washed twice with equal volumes of hot water, once with an equal volume of saturated brine solution, and then dried over sodium sulfate. The solvent was removed via an initial pass through a wiped-film evaporator still at a wall temperature of 25° to 30° C. at a pressure of 200 mm of Hg. The product was then distilled at a wall temperature of 220° C. and a pressure of 0.05 to 0.2 mm of Hg. The total distilled 9(10)-formyloctadecan-1-ol weighed 296.2 g and the residue totaled 74.1 g. The product was assayed by gas liquid chromatography (GLC).

Example 1(a) was repeated (2(a)) and comparative examples (A–D) were run as shown in Table I, below.

Preparation of 9(10)-Hydroxymethyloctadecanol

Example 1(b)

The 9(10)-formyloctadecan-1-ol from Example 1(a) was charged, along with 173 gram toluene, and 2.9 g Raney Nickel Catalyst (available as Ni-5732 P from Harshaw Chemicals), to a one liter 316 SS Autoclave.

The system was purged with nitrogen, pressurized to 500 psig with hydrogen, and heated to 140° C. The pressure was maintained between 300 and 500 psig hydrogen. After hydrogen uptake ceased, the autoclave was cooled and the product discharged through a filter press fitted with a 2 micron filter pad. The toluene was removed in vacuo to yield 287.8 g of a light yellow oil. The product was assayed by GLC.

Example 1(b) was repeated (2(b)) and comparative examples (A and D) were run as shown in Table I, below.

In Table I, the following abbreviations have the following meanings:
FO: 9(10)-formylactadecan-1-ol  C-19 Diol: 9(10)-hydroxymethyloctadecan-1-ol  TD: nonadecane-1,19-diol  C-16: hexadecan-1-ol  C-18: octadecan-1-ol

TABLE I

| | | | COMPOSITION OF PRODUCTS OF EXAMPLES | | | | |
|---|---|---|---|---|---|---|---|
| | Catalyst | | Composition (GLC Area %) | | | | |
| Run | Metal | Ligand | FO | C-19 Diol | TD | C-16 | C-18 |
| 1 | (a) Co | Acetonitrile | 73.5 | 6.7 | — | 3.8 | 4.6 |
| | (b) Co | Acetonitrile | 0.0 | 78.2 | 1.0 | 4.0 | 8.7 |
| 2 | (a) Co | Acetonitrile | 67.9 | 10.0 | — | 4.2 | 5.1 |
| | (b) Co | Acetonitrile | 3.3 | 73.4 | 1.3 | 4.6 | 8.7 |
| A | (i) Co | None | 34.7 | 27.8 | — | 4.9 | 15.9 |
| | (ii) Co | None | 0.0 | 62.9 | 5.0 | 5.6 | 19.2 |
| B | Co | Dimethylformamide | 48.5 | 13.4 | — | 4.7 | 7.5 |
| C | Co | Tributylamine | 33.1 | 25.7 | — | 5.7 | 17.6 |
| D | (i) Rh | Trilaurylphosphite | 83.3 | 0.0 | — | 3.9 | 3.7 |
| | (ii) Rh | Trilaurylphosphite | 0.0 | 82.1 | 0.2 | 3.9 | 4.9 |

What is claimed is:

1. A process for preparing a formylated olefinic fatty compound comprising reacting an olefinic fatty compound having at least 9 carbon atoms with carbon monoxide and hydrogen in the presence of a catalytic amount of a soluble cobalt salt catalyst and a promoter comprised of an organic nitrile selected from the group consisting of cyano-substituted alkanes having from 2 to 44 carbon atoms and cyano-substituted alkenes having from 4 to 22 carbon atoms containing no substituent other than cyano.

2. A process in accordance with claim 1 wherein said olefinic fatty compound is oleyl alcohol.

3. A process in accordance with claim 1 wherein said organic nitrile is acetonitrile.

4. A process in accordance with claim 1 wherein said cobalt catalyst is cobalt acetate.

5. A process in accordance with claim 1 wherein the olefinic fatty compound has at least 14 carbon atoms.

6. A process in accordance with claim 1 wherein the olefinic fatty compound has 18 carbon atoms.

7. A process in accordance with claim 1 wherein the olefinic fatty compound is a terminal olefin.

8. A process in accordance with claim 1 wherein the olefinic fatty compound is an internal olefin.

9. A process in accordance with claim 1 wherein the olefinic fatty compound is a straight-chain alkene having an internal double bond.

10. A process in accordance with claim 9 wherein the straight-chain alkene is terminally substituted with a substituent selected from the group consisting of hydroxyl, cyano, carboxyalkoxy, alkoxy, cyano-substituted alkoxy and carboxyalkoxy-substituted alkoxy.

11. A process in accordance with claim 1 wherein the organic nitrile is oleylnitrile.

12. A process for preparing 9(10)-formyloctadecan-1-ol comprising reacting oleyl alcohol with carbon monoxide and hydrogen in the presence of a catalytic amount of cobalt acetate tetrahydrate catalyst and acetonitrile.

13. A composition useful as a catalyst in preparing a formylated olefinic compound consisting of a soluble cobalt salt and an organic nitrile selected from the group consisting of cyano-substituted alkanes having from 2 to 44 carbon atoms and cyano-substituted alkenes having from 4 to 22 carbon atoms containing no substituent other than cyano.

14. A composition as defined in claim 13 wherein the mole ratio of organic nitrile to cobalt content is from about 200:1 to 1:200.

15. A composition as defined in claim 14 wherein said ratio is about 100:1.

* * * * *